United States Patent [19]

Breuer et al.

[11] 3,996,216
[45] Dec. 7, 1976

[54] 3-HETEROTHIO DERIVATIVES OF (FORMYLAMINO)ACETYLAMINO-7-ALPHA-METHOXY CEPHALOSPORINS

[75] Inventors: Hermann Breuer; Uwe D. Treuner, both of Regensburg, Germany

[73] Assignee: E. R. Squibb & Sons, Inc., Princeton, N.J.

[22] Filed: May 28, 1975

[21] Appl. No.: 581,443

[52] U.S. Cl. .................. 260/243 C; 260/519; 260/534 M; 260/332.2 A; 424/246
[51] Int. Cl.² ............ C07D 501/24; C07D 501/36; C07D 501/22
[58] Field of Search ................ 260/243 C

[56] References Cited
UNITED STATES PATENTS

| | | | |
|---|---|---|---|
| 3,766,175 | 10/1973 | Lemieux et al. | 260/243 C |
| 3,769,281 | 10/1973 | Chauvette | 260/243 C |
| 3,780,037 | 12/1973 | Hazen | 260/243 C |
| 3,819,621 | 6/1974 | Morimoto et al. | 260/243 C |
| 3,855,211 | 12/1974 | Bruer et al. | 260/243 C |

*Primary Examiner*—Nicholas S. Rizzo
*Assistant Examiner*—David E. Wheeler
*Attorney, Agent, or Firm*—Lawrence S. Levinson; Merle J. Smith

[57] ABSTRACT

3-Heterothio(formylamino)acetylamino cephalosporin derivatives of the general formula

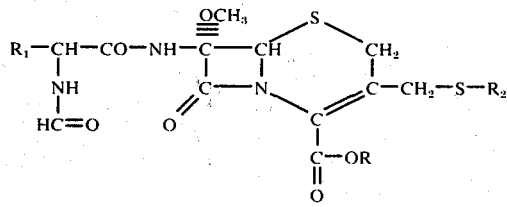

wherein R is hydrogen, lower alkyl, phenyl-lower alkyl, tri(lower alkyl)silyl, trihaloethyl, a salt forming ion or the group

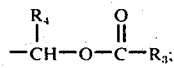

$R_1$ is hydrogen, lower alkyl, cyclo-lower alkyl, unsaturated cyclo-lower alkyl, phenyl, substituted phenyl, furyl, pyridyl or thienyl; $R_2$ is a five or six membered nitrogen, sulfur and/or oxygen containing heterocyclic ring system; $R_3$ is lower alkyl, phenyl or phenyl-lower alkyl; and $R_4$ is hydrogen or lower alkyl; are useful antibacterial agents.

10 Claims, No Drawings

3-HETEROTHIO DERIVATIVES OF (FORMYLAMINO)ACETYLAMINO-7-ALPHA-METHOXY CEPHALOSPORINS

SUMMARY OF THE INVENTION

This invention relates to new 3-heterothio-(formylamino)acetylamino-7α-methoxy cephalosporin derivatives of the formula

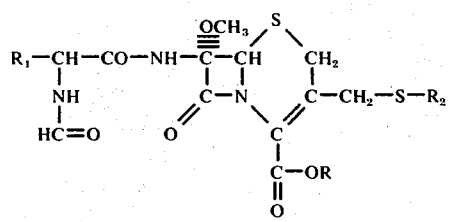

R represents hydrogen, lower alkyl, phenyl-lower alkyl, tri(lower alkyl)silyl, trihaloethyl, a salt forming ion or the group

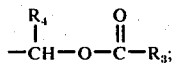

$R_1$ represents hydrogen, lower alkyl, cyclo-lower alkyl, unsaturated cyclo-lower alkyl, furyl, thienyl, pyridyl, phenyl or substituted phenyl wherein the phenyl substituents are lower alkyl, lower alkoxy, hydroxy, halogen, amino, ureido or methylsulfonylamino; $R_2$ represents a five or six-membered heterocycle including thiadiazole, oxadiazole, triazole, thiatriazole, tetrazole, 1-oxopyridine and their lower alkyl ($R_5$) substituted analogs; $R_3$ represents lower alkyl, phenyl or phenyl-lower alkyl; and $R_4$ represents hydrogen or lower alkyl.

The preferred members within each group are as follows: R is hydrogen, alkali metal or diphenylmethyl, especially hydrogen, sodium or potassium; $R_1$ is hydrogen, phenyl or thienyl, especially phenyl or thienyl; and $R_2$ is (lower alkyl)tetrazole or (lower alkyl)thiadiazole, especially wherein the lower alkyl group is methyl.

DETAILED DESCRIPTION OF THE INVENTION

The various groups represented by the symbols have the meanings defined below and these definitions are retained throughout this specification.

The lower alkyl groups are the straight and branched chain hydrocarbon groups in the series from methyl to heptyl, the $C_1$ to $C_4$ members and especially methyl and ethyl being preferred. The lower alkoxy groups are of the same kind.

The phenyl-lower alkyl radicals include a phenyl ring attached to a lower alkyl group of the kind described above as well as those containing two phenyl groups such as diphenylmethyl, benzyl and diphenylmethyl being preferred.

The salt forming ions represented by R are metal ions, e.g., alkali metal ions such as sodium or potassium, alkaline earth metal ions such as calcium or magnesium, or an amine salt ion, e.g., a (lower alkyl)amine like methylamine or triethylamine or a cyclo-lower alkylamine, like dicyclohexylamine, etc.

The halogens are the four common halogens, of which chlorine and bromine are preferred. In the case of the trihaloethyl group represented by R,2,2,2-trichloroethyl is preferred.

Trimethylsilyl is the preferred tri(lower alkyl)silyl group.

$R_2$ is thiadiazole, oxadiazole, triazole, thiatriazole, tetrazole, 1-oxopyridine and the lower alkyl substituted analogs of each of these except 1-oxopyridine and thiatriazole, especially 1,3,4-thiadiazole, 1,2,4-thiadiazole, tetrazole, 5-methyl-1,3,4-thiadiazol-2-yl, 3-methyl-1,2,4-thiadiazol-5-yl and 1-methyl-tetrazol-5-yl. The heterocyclics have, in particular, these structures:

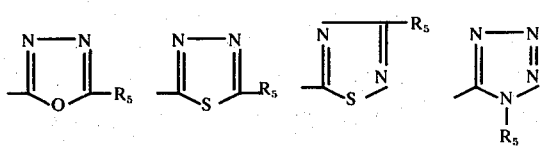

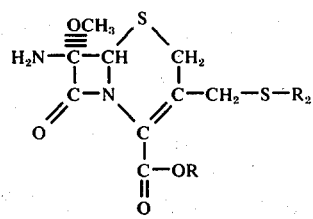

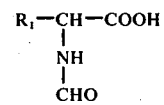

wherein $R_5$ is hydrogen or lower alkyl, especially methyl.

The new cephalosporin derivatives of this invention are produced by several methods. According to one method, a 7-amino-7α-methoxy cephalosporanic acid (7α-methoxy-7-ACA) derivative of the formula

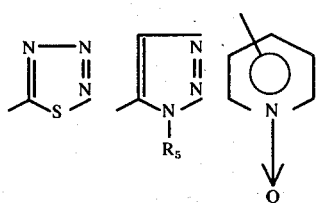

is reacted with an acid of the formula $$R_1-CH-COOH \quad (III)$$
$$|$$
$$NH$$
$$|$$
$$CHO$$

or an activated derivative like an activated ester or mixed anhydride, and/or in the presence of a coupling agent like dicyclohexylcarbodiimide.

One preferred synthesis comprises reacting the acid of formula III with the diphenylmethyl ester of the 7α-methoxy-7-ACA derivative of formula II in the presence of dicyclohexylcarbodiimide and then hydrolyzing the ester with trifluoroacetic acid and anisole to obtain the free carboxyl group in the 4-position. A salt can be obtained from the acid by reaction with the base having the desired cation.

The reaction between the 7-amino-7α-methoxycephalosporanic acid compound and the acid of formula III can be carried out, for example, by dissolving or suspending the acid in an inert organic solvent such as chloroform, tetrahydrofuran, methylene chloride, dioxane, benzene or the like, and adding, at a reduced temperature of about 0°–5° C., about an equimolar amount of the 7α-methoxy-7-ACA compound in the presence of a coupling agent such as dicyclohexylcarbodiimide. The product of the reaction is then isolated by conventional procedures, e.g., by concentration or evaporation of the solvent. If a derivative of the 7α-methoxyaminocephalosporanic acid compound, such as the diphenylmethyl ester is used, the free acid is obtained by hydrolysis, e.g., with trifluoroacetic acid and anisole or the like. Salts can then be derived from the free acid.

According to another embodiment, an acid of formula III is reacted with a compound of the formula

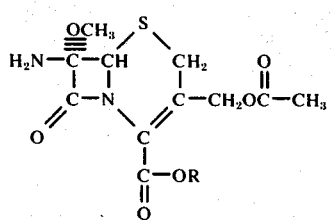 (IV)

preferably wherein R is diphenylmethyl. When R is the preferred diphenylmethyl group, it is converted to the free acid with trifluoroacetic acid and anisole. The product of formula V (which is the subject of our copending application Ser. No. 581,442 filed simultaneously herewith)

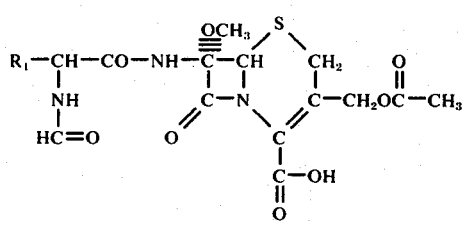 (V)

is then reacted with a thiol of the formula
 (VI)

in a basic solution, e.g., at a pH of about 7.8, to obtain the product of formula I.

According to still another embodiment, a compound of the formula

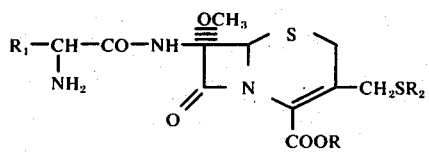 (VII)

is formylated, for example with formic acid and acetic anhydride or other formylating agent.

When R is the acyloxymethyl group

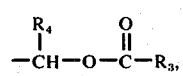

this group can be introduced into the 7α-methoxy-7-aminocephalosporanic acid moiety prior to the reaction with the acid of formula III or the activated derivative by treatment with one to two moles of a halomethyl ester of the formula

 (VIII)

wherein hal is halogen, preferably chlorine or bromine, in an inert organic solvent such as dimethylformamide, acetone, dioxane, benzene or the like, at about ambient temperature or below.

The acid of formula III is produced by reacting an α-amino acid of the formula

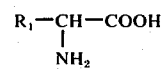 (IX)

with a formylating agent, e.g., formic acid and acetic anhydride, which is preferred, phenyl formate, p-nitrophenyl formate, etc., at a temperature of about 0°–5° C.

Further process details are also provided in the illustrative examples. Starting materials of formulas II, IV and VII are produced by the methods described in British Pat. Nos. 1,348,984 and 1,348,987, Mar. 27, 1974, and Belgian Pat. No. 768528, Dec. 15, 1971.

Certain of the compounds of this invention may exist in different optically active forms. The various stereoisomeric forms as well as the racemic mixtures are within the scope of the invention.

The compounds of this invention have a broad spectrum of antibacterial activity against both gram positive and gram negative organisms such as *Staphylococcus aureus, Salmonella schottmuelleri, Pseudomonas aeruginosa, Proteus vulgaris, Escherichia coli* and *Streptococcus pyogenes*. They are useful as antibacterial agents, e.g., to combat infections due to organisms such as those named above, and in general they can be utilized in a manner similar to cephradine and other cephalosporins. For example, a compound of formula I or a physiologically acceptable salt thereof can be used in various animal species affected by infections of such bacterial origin in an amount of about 1 to 75 mg/kg daily, orally or parenterally, in single or two to four divided doses.

Up to about 500 mg. of a compound of formula I or a physiologically acceptable salt thereof is administered by incorporating in an oral dosage form such as tablets, capsules or elixirs or in an injectable form in a sterile aqueous vehicle prepared according to conventional pharmaceutical practice.

The following examples are illustrative of the invention. All temperatures are in degrees celsius. Additional variations are produced in the same manner by appropriate substitution in the starting material.

EXAMPLE 1

7α-Methoxy-3-[[(5-methyl-1,3,4-thiadiazol-2-yl)thio]methyl]-7-amino-8-oxo-5-thia-1-azabicyclo[4.2.0]oct-2-ene-2-carboxylic acid A mixture of 15.1 g. (0.05 M) of 7-amino-7α-methoxycephalosporanic acid in 100 ml. of water and 50 ml. of acetone are brought to pH 8 with sodium hydroxide while stirring. 7.5 g. (0.057 M) of 2-methyl-1,3,4-thiadiazole-5-thiol are added and the mixture is heated at 80° for 4 hours. After cooling to 5°, this is acidified to pH 3.5 with dilute hydrochloric acid and stirred for 15 minutes. The precipitated solid is filtered under suction and washed with acetone. This 3-[[(5-methyl-1,3,4-thiadiazol-2-yl)thio]-methyl]-7-amino-7α-methoxy-8-oxo-5-thia-1-azabicyclo[4.2.0]oct-2-ene-2-carboxylic acid is purified by dissolving in sodium bicarbonate solution and reprecipitating with 2N hydrochloric acid.

EXAMPLE 2

3-[[(3-methyl-1,2,4-thiadiazol-5-yl)thio]methyl]-7-amino-7α-methoxy-8-oxo-5-thia-1-azabicyclo[4.2.0]oct-2-ene-2-carboxylic acid By substituting 3-methyl-1,2,4-thiadiazole-5-thiol for the 2-methyl-1,3,4-thiadiazole-5-thiol in the procedure of Example 1, 3-[[(3-methyl-1,2,4-thiadiazol-5-yl)thiol]-methyl]-7-amino-7α-methoxy-8-oxo-5-thia-1-azabicyclo[4.2.0]-oct-2-ene-2-carboxylic acid is obtained.

EXAMPLE 3

3-[[(1-Methyl-1H-tetrazol-5-yl)thio]methyl]-7-amino-7α-methoxy-8-oxo-5-thia-1-azabicyclo[4.2.0]oct-2-ene-2-carboxylic acid By substituting 0.057 M of 1-methyl-1H-tetrazole-5-thiol for the 2-methyl-1,3,4-thiadiazol-5-thiol in the procedure of Example 1, 3-[[(1-methyl-1H-tetrazol-5-yl)thiol]-methyl]-7-amino-7α-methoxy-8-oxo-5-thia-1-azabicyclo[4.2.0]-oct-2-ene-2-carboxylic acid is obtained.

EXAMPLE 4

7-Amino-7α-methoxy-3-[[(5-methyl-1,3,4-thiadiazol-2-yl)thio]-methyl]-8-oxo-5-thia-1-azabicyclo[4.2.0]oct-2-ene-2-carboxylic acid, diphenylmethyl ester 18 g. of 7-amino-7α-methoxy-3-[[(5-methyl-1,3,4-thiadiazol-5-yl)thio]methyl]-8-oxo-5-thia-1-azabicyclo[4.2.0]oct-2-ene-2-carboxylic acid are suspended in 350 ml. of tetrahydrofuran. 4.1 ml. of 70% perchloric acid are added dropwise. After 30 minutes, a slightly turbid solution forms. This solution is filtered and to the filtrate is added dropwise with stirring 12 g. of diphenyldiazomethane and 20 ml. of tetrahydrofuran. Afer 3 hours, the reaction mixture is poured into 2 liters of absolute ether. The solid, light brown precipitate, which is the perchloric acid salt of the desired product, is dried over Kieselgel in a desiccator. To obtain the base, the perchloric acid salt is dissolved in water and treated with the calculated equivalent of potassium bicarbonate. The aqueous solution obtained is extracted with chloroform. The chloroform phase is treated with activated carbon and sodium sulfate to obtain 10 g. of the product, 7-amino-7α-methoxy-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester. The product is recrystallized from tetrahydrofuran/petroleum ether.

7-Amino-7α-methoxy-3-[[(3-methyl-1,2,4-thiadiazol-5-yl)thio]methyl]-8-oxo-5-thia-1-azabicyclo[4.2.0]oct-2-ene-2-carboxylic acid, diphenylmethyl ester is similarly obtained by substituting the product of Example 2.

EXAMPLE 5

7-Amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester The product, 7-amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester, is obtained by the procedure of Example 4 utilizing as starting material 7-amino-7α-methoxy-3-[[(1-methyl-1H-tetrazol-5-yl)thio]methyl]-8-oxo-5-thia-1-azabicyclo[4.2.0]oct-2-ene-2-carboxylic acid.

EXAMPLE 6 a.

7β-[[[[(4-Methoxyphenyl)methoxy]carbonyl]amino]phenyl-acetyl]amino]-7α-methoxy-3-[[(1-methyl-1H-tetrazol-5-yl)-thio]methyl]-8-oxo-5-thia-1-azabicyclo[4.2.0]oct-2-ene-2-carboxylic acid, diphenylmethyl ester 3.78 g. (0.012 mol.) of [[[(4-methoxyphenyl)methoxy]carbonyl]amino]benzeneacetic acid (prepared as described in U.S. Pat. No. 3,560,489, Feb. 2, 1971) are dissolved in 100 ml. of tetrahydrofuran and added to a solution of 5.27 g. (0.01 mol.) of 7-amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester in 50 ml. of methylene chloride. The mixture is cooled to 0°–5° and at this temperature a solution of 2.27 g. (0.011 mol.) of dicyclohexylcarbodiimide is added dropwise. The mixture is stirred for 90 minutes at 0°–5° and 90 minutes at room temperature. The precipitated dicyclohexylurea is filtered off. The filtrate is concentrated and the residue is taken up in a mixture of ethyl acetate and tetrahydrofuran (3:1). The organic phase is washed once with sodium bicarbonate solution and twice with water, then decolorized with activated carbon, dried with magnesium sulfate, filtered and concentrated to a small volume. The precipitated product is filtered under suction. 7α-methoxy-7β-[[[[(4-methoxyphenyl)methoxy]carbonyl]amino]phenyl-acetyl]amino]-3-[[(1-methyl-1H-tetrazol-5-yl)thio]methyl]-8-oxo-5thia-1-azabicyclo[4.2.0]oct-2-ene-2-carboxylic acid, diphenylmethyl ester is obtained. By concentrating the mother liquor and adding ether, additional product is obtained.

b.

7β-[(aminophenylacetyl)amino]-7α-methoxy-3-[[(1-methyl-1H-tetrazol-5-yl)thio]methyl]-8-oxo-5-thia-1-azabicyclo[4.2.0]-oct-2-ene-2-carboxylic acid, trifluoroacetic salt 3.7 g. of the product of part a are added at 0°–5° to a mixture of 74 ml. of trifluoroacetic acid and 22 ml. of anisole. After 10 minutes, the trifluoroacetic acid is evaporated under vacuum and ether is added to the residue.

7β-[(aminophenylacetyl)amino]-7α-methoxy-3-[[(1-methyl-1H-tetrazol-5-yl)thio]methyl]-8-oxo-5-thia-azabicyclo[4.2.0]oct-2-ene-2-carboxylic acid, trifluoroacetic salt is obtained.

EXAMPLE 7

D-α-[[[(4-methoxyphenyl)methoxy]carbonyl]amino]-2-thiopheneacetic acid 8.0 g. of magnesium oxide are suspended in 200 ml. of water. 15.7 g. of D-2-(2-thienyl)glycine are added to the suspension followed by a solution of 22.8 g. of p-methoxybenzyloxycarbonylazide in 200 ml. dioxane. The mixture is stirred for 3 days at room temperature.

The reaction mixture is then filtered and the filtrate is extracted once with 125 ml. of diethyl ether. The ether layer is then discarded. The aqueous phase is cooled to 5°–10°, layered with about 150 ml. of ethyl acetate and acidified with 2N hydrochloric acid to pH 2.5. After separating the layers, the aqueous phase is extracted again with 100 ml. of ethyl acetate. The combined ethyl acetate solutions are washed once with water, dried over magnesium sulfate and evaporated. The oily residue crystallizes on treatment with petroleum ether. The yield amounts to 30.8 gms. of crude material. After recrystallization from ethyl acetate/petroleum ether, 25.2 gms. of D-α-[[[(4-methoxyphenyl)methoxy]carbonyl]amino]-2-thiopheneacetic acid are obtained, m.p. 66°–69°. The material is usually contaminated with a small amount of ethyl acetate which cannot be removed at 35° in vacuum. The material obtained free from ethyl acetate has a melting point 89°–92° $[\alpha]_D^{25} = 62.2°$ ($c = 1$, tetrahydrofuran).

EXAMPLE 8

7α-methoxy-7β-[[[[(4-methoxyphenyl)methoxy]carbonyl]amino]-(2-thienyl)-acetyl]amino]-3-[[(1-methyl-1H-tetrazol-5-yl)thio]methyl]-8-oxo-5-thia-1-azabicyclo[4.2.0]oct-2-ene-2-carboxylic acid, diphenyl ester The product of Example 7 and 7-amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester are dissolved in 650 ml. of absolute tetrahydrofuran and the solution is cooled to 0°. At this temperature, a solution of 7.3 gms. of dicyclohexylcarbodiimide in 60 ml. of absolute tetrahydrofuran is added dropwise over a period of about 20 minutes. The mixture is stirred at 0° for 2 hours and an additional two hours at room temperature. The dicyclohexylurea which precipitates is removed by filtration. The filtrate is concentrated in vacuum. The residue is dissolved in ethyl acetate, washed with saturated sodium bicarbonate solution, then with water and dried with magnesium sulfate. After filtration, the filtrate is left overnight in the refrigerator. The reaction product crystallizes. On filtration, 7α-methoxy-7β-[[[[[(4-methoxyphenyl)methoxy]carbonyl]amino]-2-(2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester is obtained. The filtrate is evaporated to dryness.

EXAMPLE 9

7-[D-2-amino-2-(2-thienyl)acetamido]-7α-methoxy-3-[[(1-methyl-1H-tetrazol-5-yl)thio]methyl]-8-oxo-5-thia-1-azabicyclo[4.2.0]oct-2-ene-2-carboxylic acid, trifluoroacetate salt 11.5 gms. of the product of Example 8 are mixed with 30 ml. of anisole, cooled to 0°–5° and 150 ml. of trifluoroacetic acid are added. The solution is stirred to 10 minutes at this temperature. Then the solvent is stripped off in vacuum and the residue is treated with diethyl ether. 8.6 gms. of 7-[D-2-amino-2-(2-thienyl)acetamido]-7α-methoxy-3-[[(1-methyl-1H-tetrazol-5-yl)thio]methyl]-8-oxo-5-thia-1-azabicyclo[4.2.0]oct-2-ene-2-carboxylic acid, trifluoroacetate salt are obtained.

EXAMPLE 10

α-(Formylamino)benzeneacetic acid 40.8 ml. of acetic anhydride are cooled to 0°–5° and 54.4 ml. of formic acid are added dropwise with stirring at this temperature. The mixture is let stand for 30 minutes at this temperature and then 15.2 g. (0.1 mol.) of D-phenylglycine are added. After about 10 minutes, a clear solution results and after an additional 15 minutes α-(formylamino)benzeneacetic acid crystallizes. The temperature is allowed to rise to room temperature and 300 ml. of ice water are added. The mixture is then stirred for five minutes, filtered under suction, washed with water and dried, yield 11.4 g., m.p. 170°–175°. The product, α-(formylamino)benzeneacetic acid, is recrystallized from ethanol. The melting point remains unchanged.

EXAMPLE 11

3-[(Acetyloxy)methyl]-7β-[[(formylamino)phenylacetyl]amino]-7α-methoxy-8-oxo-5-thia-1-azabicyclo[4.2.0]oct-2-ene-2-carboxylic acid, diphenylmethyl ester 2.15 g. (0.012 mol.) of α-(formylamino)benzeneacetic acid are brought into solution at 40° in 200 ml. of anhydrous tetrahydrofuran. After cooling to room temperature, 4.7 g. (0.01 mol.) of 7-amino-7α-methoxycephalosporanic acid, diphenylmethyl ester are added and the solution is cooled to 0°–5°. A solution of 2.27 g. (0.011 mol.) of dicyclohexylcarbodiimide in 20 ml. of tetrahydrofuran is added dropwise over a period of 20 minutes and the mixture is stirred for 90 minutes at 0°–5° and then 90 minutes at room temperature. This is then filtered and the filtrate is concentrated. The residue is taken up in a mixture of 250 ml. of ethyl acetate and 100 ml. of tetrahydrofuran, shaken with dilute sodium bicarbonate solution and with water, dried with magnesium sulfate and concentrated to about one-fourth the original volume. Upon standing in the refrigerator overnight, 3-[(acetyloxy)methyl]-7β-[[(formylamino)phenylacetyl]amino]-7α-methoxy-8-oxo-5-thia-1-azabicyclo[4.2.0]oct-2-ene-2-carboxylic acid, diphenylmethyl ester crystallizes.

EXAMPLE 12

3-[(Acetyloxy)methyl]-7β-[[(formylamino)phenylacetyl]amino]-7α-methoxy-8-oxo-5-thia-1-azabicyclo[4.2.0]oct-2-ene-2-carboxylic acid 3.8 g. of 3-[(acetyloxy)methyl]-7β-[[(formylamino)phenylacetyl]amino]-7α-methoxy-8-oxo-5-thia-1- azabicyclo[4.2.0]oct-2-ene-2-carboxylic acid, diphenylmethyl ester are added to a mixture of 76 ml. of trifluoroacetic acid and 24 ml. of anisole at 0°–5°. This is stirred at this temperature for 10 minutes and then concentrated. After the addition of ether, the solid material is filtered under suction. 3-[(acetyloxy)methyl]-7β-[[(formylamino)phenylacetyl]amino]-7α-methoxy-8-oxo-5-thia-1-azabicyclo[4.2.0]oct-2-ene-2-carboxylic acid is obtained.

EXAMPLE 13

3-[(Acetyloxy)methyl]-7β-[[(formylamino)-phenylacetyl]amino]-7α-methoxy-8-oxo-5-thia-1-azabicyclo[4.2.0]oct-2-ene-2-carboxylic acid sodium salt 2.15 g. (0.005 mol.) of 3-[(acetyloxy)methyl]-7β-[[(formylamino)phenylacetyl]amino]-7α-methoxy-8-oxo-5-thia-1-azabicyclo[4.2.0]oct-2-ene-2-carboxylic acid are suspended in 50 ml. of water and the suspension is stirred with 50 ml. of 0.1N sodium bicarbonate until the substance is almost completely dissolved. This is filtered and freeze dried. 3-[(acetyloxy)methyl]-7β-[[(formylamino)phenylacetyl]amino]-7α-methoxy-8-oxo-5-thia-1-azabicyclo[4.2.0]oct-2-ene-2-carboxylic acid, sodium salt is obtained.

EXAMPLE 14

D-α-(Formylamino)-2-thiopheneacetic acid

D-α-amino-2-thiopheneacetic acid is made to react with formic acid and acetic anhydride by the procedure of Example 10 to obtain D-α-(formylamino)-2-thiopheneacetic acid, m.p. 134°–135° (dec.).

EXAMPLE 15

D-7β-[[(Formylamino)-(2-thiophene)acetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester D-α-(formylamino)-2-thiopheneacetic acid and 7-amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester are made to react in the presence of dicyclohexylcarbodiimide by the procedure of Example 11 to obtain D-7β-[[(formylamino)-(2-thiophene)acetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester.

EXAMPLE 16

D-7β-[[(Formylamino)-(2-thiophene)acetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid The product of Example 15 is treated with trifluoroacetic acid and anisole according to the procedure of Example 12 to obtain D-7β-[[(formylamino)-(2-thiophene)acetyl]-amino]-7α-methoxy-3-[[(1-methyl-1H-tetrazol-5-yl)thio]methyl]-8-oxo-5-thia-1-azabicyclo[4.2.0]oct-2-ene-2-carboxylic acid which is dissolved with aqueous sodium bicarbonate solution, filtered and purified by precipitation with 2N hydrochloric acid.

EXAMPLE 17

D-7β-[[(Formylamino)-(2-thiophene)acetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid, potassium salt 1.4 g. of the product of Example 16 are dissolved in 35 ml. of methanol and a 2N solution of potassium ethylhexanoate and n-butanol is added. This is filtered and the product, D-7β-[[(formylamino)-(2-thiophene)acetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid, potassium salt is precipitated by the addition of ether.

EXAMPLE 18

7α-Methoxy-7β-[[[[(4-methoxyphenyl)methoxy]carbonyl]amino]phenylacetyl]amino]-3-(hydroxymethyl)-8-oxo-5-thia-1-azabicyclo [4.2.0]oct-2-ene-2-carboxylic acid-3-acetate, diphenylmethyl ester 2.35 g. (0.05 mol.) of 7-amino-7α-methoxycephalosporanic acid, diphenylmethyl ester are dissolved in 250 ml. of methylene chloride and a solution of 18.92 g. (0.06 mol.) of α-[[[(4-methoxyphenyl)methoxy]carbonyl]amino]-2-benzeneacetic acid (prepared from phenylglycine, p-methoxybenzyloxy carbonyl azide and magnesium oxide) in 500 ml. of tetrahydrofuran is added. The mixture is cooled to 0°–5° and a solution of 11.4 g. (0.055 mol.) of dicyclohexylcarbodiimide in 100 ml. of tetrahydrofuran is added dropwise. The reaction mixture is stirred for 90 minutes at 0°–5° and 90 minutes at room temperature. This is then filtered, the filtrate is washed with sodium bicarbonate solution and with water and concentrated. The residue is treated with ethyl acetate. 7α-methoxy-7β-[[[[(4-methoxyphenyl)methoxy]carbonyl]amino]-phenylacetyl]amino]-3-(hydroxymethyl)-8-oxo-5-thia-1-azabicyclo[4.2.0]oct-2-ene-2-carboxylic acid-3-acetate, diphenylmethyl ester crystallizes.

EXAMPLE 19

7-[(2-Amino-2-phenylacetyl)amino]-3-(hydroxymethyl)-7α-methoxy-8-oxo-5-thia-1-azabicyclo[4.2.0]oct-2-ene-2-carboxylic acid trifluoroacetic acid salt 3.7 g. of the product of Example 18 are added to a mixture of 74 ml. of trifluoroacetic acid and 22 ml. of anisole at 0°–5°. This is stirred for 10 minutes and concentrated. Ether is added to the residue to obtain 7-[(2-amino-2-phenylacetyl)amino]-3-(hydroxymethyl)-7α-methoxy-8-oxo-5-thia-1-azabicyclo[4.2.0]oct-2-ene-2-carboxylic acid trifluoroacetic acid salt.

EXAMPLE 20

3-[(Acetyloxy)methyl]-7β-[[(formylamino)-phenylacetyl]amino]-7α-methoxy-8-oxo-5-thia-1-azabicyclo[4.2.0]oct-2-ene-2-carboxylic acid The product of Example 19 is made to react with formic acid and acetic anhydride according to the procedure of Example 10 to obtain 3-[(acetyloxy)methyl]-7β-[[(formylamino)phenylacetyl]amino]-7α-methoxy-8-oxo-5-thia-1-azabicyclo[4.2.0]oct-2-ene-2-carboxylic acid.

EXAMPLE 21

7β-[[(formylamino)phenylacetyl]amino]-7α-methoxy-3-[[(1-oxo-2-pyridinyl)thio]methyl]-8-oxo-5-thia-1-azabicyclo[4.2.0]oct-2-ene-2-carboxylic acid 0.01 mol. of 3-[(acetyloxy)methyl]-7β-[[(formylamino)-phenylacetyl]amino]-7α-methoxy-8-oxo-5-thia-1-azabicyclo[4.2.0]oct-2-ene-2-carboxylic acid, sodium salt (Example 13) is dissolved in 100 ml. of water, 0.011 mol. of 1-oxopyridine-2-thiol, sodium salt is added and the solution is heated at 60° (pH ~ 7.5) for 3 hours. After cooling, the solution is acidified with 2N hydrochloric acid to pH 1.5 and filtered under suction. 7β-[[(formyl)phenylacetyl]amino]-7α-methoxy-3-[[(1-oxo-2-pyridinyl)thiomethyl-8-oxo-5-thia-1-azabicyclo[4.2.0]oct-2-ene-2-carboxylic acid is obtained.

EXAMPLES 22–49

The products below are obtained by the procedure of Examples 15 and 16 (Example 17 to obtain the salt) from the α-formylamino acetic acid

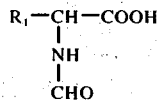

and the diphenylmethyl ester of one of the following [produced by the procedure of Examples 1 and 4]:

a. 3-[[(5-methyl-1,3,4-thiadiazol-2-yl)thio]methyl]-7-amino-7α-methoxy-8-oxo-5-thia-1-azabicyclo[4.2.0]oct-2-ene-2-carboxylic acid
b. 3-[[(1-methyl-1H-tetrazol-5-yl)thio]methyl]-7α-methoxy-7-ACA
c. 3-[[(1,3,4-oxadiazol-2-yl)thio]methyl]-7α-methoxy-7-ACA
d. 3-[[(5-ethyl-1,3,4-oxadiazol-2-yl)thio]methyl]-7α-methoxy-7-ACA
e. 3-[[(1,2,3,4-tetrazol-5-yl)thio]methyl]-7α-methoxy-7-ACA
f. 3-[[(1-ethyl-1H-tetrazol-5-yl)thio]methyl]-7α-methoxy-7-ACA
g. 3-[[(1,2,4-thiadiazol-3-yl)thio]methyl]-7α-methoxy-7-ACA
h. 3-[[(5-butyl-1,2,4-thiadiazol-3-yl)thio]methyl]-7α-methoxy-7-ACA
i. 3-[[(3-methyl-1,2,4-oxadiazol-5-yl)thio]methyl]-7α-methoxy-7-ACA
j. 3-[[(2-methyl-1,3,4-thiadiazol-5-yl)thio]methyl]-7α-methoxy-7-ACA
k. 3-[[(1,2,4-thiadiazol-5-yl)thio]methyl]-7α-methoxy-7-ACA
l. 3-[[(5-methyl-1,2,4-thiadiazol-2-yl)thio]methyl]-7α-methoxy-7-ACA
m. 3-[[(2-methyl-1H-tetrazol-5-yl)thio]methyl]-7α-methoxy-7-ACA
n. 3-[[(1,3,4-thiadiazol-2-yl)thio]methyl]-7α-methoxy-7-ACA
o. 3-[[(1,2,3,4-thiatriazol-5-yl)thio]methyl]-7α-methoxy-7-ACA
p. 3-[[(1,2,3-thiazol-5-yl)thio]methyl]-7α-methoxy-7-ACA
q. 3-[[(1-methyl-1,2,3-thiazol-5-yl)thio]methyl]-7α-methoxy-7-ACA
r. 3-[[(1-oxopyridin-2-yl)thio]methyl]-7α-methoxy-7-ACA
s. 3-[[(1-oxopyridin-3-yl)thio]methyl]-7α-methoxy-7-ACA

EXAMPLE

21 D-7β-[[α-formylamino)phenylacetyl]amino-7α-methoxy-3-[[(1,3,4-thiadiazol-2-yl)thio]methyl]-8-oxo-5-thia-1-azabicyclo[4.2.0]oct-2-ene-2-carboxylic acid 22 D-7β-[[(α-formylamino)acetyl]amino]-7α-methoxy-3-[[(1,3,4-oxodiazol-2-yl)thio]methyl]-8-oxo-5-thia-1-azabicyclo[4.2.0]oct-2-ene-2-carboxylic Example acid 23 D-7β-[[(α-formylamino)propionyl]amino]-3-[[(5-ethyl-1,3,4-oxadiazol-2-yl)thio]methyl]-7α-methoxy-8-oxo-5-thia-1-azabicyclo[4.2.0]oct-2-ene-2-carboxylic acid 24 D-7β-[[(α-formylamino)acetyl]amino]-7α-methoxy-3-[[(1,2,4-thiadiazol-5-yl)thio]methyl]-8-oxo-5-thia-1-azabicyclo[4.2.0]oct-2-ene-2-carboxylic acid 25 D-7β-[[(α-formylamino)butyryl]amino]-7α-methoxy-3-[[(1,2,4-thiadiazol-3-yl)thio]methyl]-8-oxo-5-thia-1-azabicyclo[4.2.0]oct-2-ene-2-carboxylic acid 26 D-7β-[[(α-formylamino)phenylacetyl]amino]-3-[[(5-butyl-1,2,4-thiadiazol-3-yl)thio]methyl]-7α-methoxy-8-oxo-5-thia-1-azabicyclo[4.2.0]oct-2-ene-2-carboxylic acid 27 D-7β-[[(α-formylamino)phenylacetyl]amino]-7α-methoxy-3-[[(1,2,3,4-tetrazol-5-yl)thio]methyl]-8-oxo-5-thia-1-azabicyclo[4.2.0]oct-2-ene-2-carboxylic acid 28 D-7β-[[(α-formylamino)cyclohexylacetyl]amino]-7α-methoxy-3-[[(3-methyl-1,2,4-oxadiazol-5-yl)thio]methyl]-8-oxo-5-thia-1-azabicyclo[4.2.0]oct-2-ene-2-carboxylic acid 29 D-7β-[[(α-formylamino)-1-cyclohexen-1-yl-acetyl]amino]-3-[[(1-ethyl-1H-tetrazol-5-yl)thio]-methyl-7α-methoxy-8-oxo-5-thia-1-azabicyclo[4.2.0]oct-2-ene-2-carboxylic acid 30 D-7β-[[α-formylamino)cyclopentylacetyl]amino]-3-[[(1-ethyl-1H-tetrazol-5-yl)thio]methyl]-7α-methoxy-8-oxo-5-thia-1-azabicyclo[4.2.0]oct-2-ene-2-carboxylic acid Example 31 D-7β-[[α-formylamino)-(2-thiophene)acetyl]amino]-7α-methoxy-3-[[2-(2-methyl-1,3,4-thiadiazol-5-yl)thio]methyl]-8-oxo-5-thia-1-azabicyclo[4.2.0]oct-2-ene-2-carboxylic acid 32 D-7β-[[(α-formylamino)-(1,4-cyclohexadien-1-yl)-acetyl]amino]-7α-methoxy-3-[[(5-methyl-1,3,4-thiadiazol-2-yl)thio]methyl]-8-oxo-5-thia-1-azabicyclo[4.2.0]oct-2-ene-2-carboxylic acid and potassium salt 33 D-7β-[[(α-formylamino)-(p-tolyl)acetyl]amino]-7α-methoxy-3-[[(1,3,4-oxadiazol-2-yl)thio]methyl]-8-oxo-5-thia-1-azabicyclo[4.2.0]oct-2-ene-2-carboxylic acid and sodium salt 34 D-7β-[[(α-formylamino)-(2-hydroxyphenyl)acetyl]amino]-3-[[(5-ethyl-1,3,4-oxadiazol-2-yl)thio]methyl]-7α-methoxy-8-oxo-5-thia-1-azabicyclo[4.2.0]oct-2-ene-2-carboxylic acid 35 DL-7β-[[(α-formylamino)-(4-hydroxyphenyl)acetyl]amino]-7α-methoxy-3-[[(1,2,3,4-tetrazol-5-yl)thio]methyl]-8-oxo-5-thia-1-azabicyclo[4.2.0]oct-2-ene-2-carboxylic acid, phenyl ester 36 D-7β-[[α-formylamino)-(4-ureidophenyl)acetyl]amino]-7α-methoxy-3-[[(1,2,4-thiadiazol-5-yl)thio]- methyl]-8-oxo-5-thia-1-azabicyclo[4.2.0]oct-2-ene-2-carboxylic acid, triethylamine salt 37    D-7β-[[(α-formylamino)-(4-methylsulfonylamino)phenyl-acetyl]amino]-7α-methoxy-3-[[(1,2,4-thiadiazol-3-yl)thio]methyl]-8-oxo-5-thia-1-azabicyclo[4.2.0]oct-2-ene-2-carboxylic acid pivaloyloxy methyl ester Example 38    D-7β-[[α-formylamino)-(2-chlorophenyl)acetyl]amino]-7α-methoxy-3-[[2-methyl-1,3,4-thiadiazol-5-yl)thio]-methyl]-8-oxo-5-thia-1-azabicyclo[4.2.0]oct-2-enc-2-carboxylic acid trimethylsilyl ester 39    D-7α-[[(α-formylamino)-(3-thiophene)acetyl]amino]-7α-methoxy-3-[[(5-methyl-1,2,4-thiadiazol-2-yl)thio]methyl]-8-oxo-5-thia-1-azabicyclo[4.2.0]oct-2-ene-2-carboxylic acid, (1-acetyloxy)ethyl ester 40    D-7β-[[(α-formylamino)-(2-furanyl)acetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid diphenylmethyl ester 41    D-7β-[[(α-formylamino)phenylacetyl[amino]-7α-methoxy-3-[[1,2,3,4-thiatriazol-5-yl)thio]methyl]-8-oxo-5-thia-1-azabicyclo[4.2.0]oct-2-ene-2-carboxylic acid, 2,2,2-trichloroethyl ester 42    D-7β-[[(α-formylamino)acetyl]amino]-7α-methoxy-3-[[(1,2,3-triazol-5-yl)thio]methyl]-8-oxo-5-thia-1-azabicyclo[4.2.0]oct-2-ene-2-carboxylic acid 43    D-7β-[[(α-formylamino)-(1,4-cyclohexadien-1-yl)acetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid, methyl ester 44    D-7β-[[(α-formylamino)-(2-thiophene)acetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid, benzyl ester 45    DL-7β-[[(α-formylamino)phenylacetyl]amino]-7α-methoxy-3-[[(1-methyl-1,2,3-triazol-5-yl)thio]methyl]-8-oxo-5-thia-1-azabicyclo[4.2.0]oct-2-ene-2-carboxylic acid and potassium salt Example 46    DL-7β-[[(α-formylamino)-(2-pyridyl)acetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid 47    D-7β-[[(α-formylamino)phenylacetyl]amino]-7α-methoxy-3-[[1-oxopyridin-2-yl)thio]methyl]-8-oxo-5-thia-1-azabicyclo[4.2.0]oct-2-ene-2-carboxylic acid and sodium salt 48    DL-7β-[[(α-formylamino)acetyl]amino]-7α-methoxy-3-[[1-oxopyridin-3-yl)thio]methyl]-8-oxo-5-thia-1-azabicyclo[4.2.0]oct-2-ene-2-carboxylic acid

What is claimed is:

1. A compound of the formula

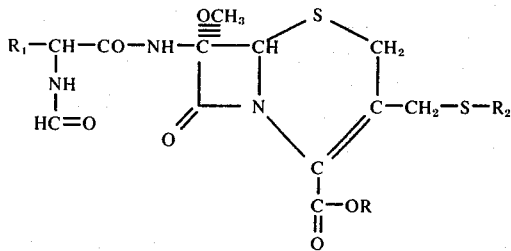

wherein R is hydrogen, lower alkyl, phenyl-lower alkyl, tri(lower alkyl)silyl, trihaloethyl,

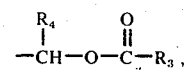

alkali metal, alkaline earth metal or (lower alkyl)amine; $R_1$ is thienyl or phenyl; $R_2$ is $R_5$-thiadiazole, $R_5$-oxadiazole, $R_5$-triazole, thiatriazole, $R_5$-tetrazole or 1-oxopyridine; $R_3$ is lower alkyl, phenyl or phenyllower alkyl; and $R_4$ and $R_5$ each is hydrogen or lower alkyl.

2. A compound as in claim 1 wherein $R_1$ is phenyl.

3. A compound as in claim 1 wherein $R_1$ is thienyl.

4. A compound as in claim 1 wherein $R_2$ is 1-methyltetrazole.

5. A compound as in claim 1 wherein $R_2$ is methylthiadiazole.

6. A compound of the formula

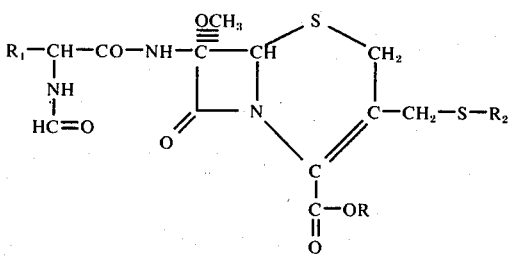

wherein R is hydrogen, alkali metal or diphenylmethyl; $R_1$ is phenyl or thienyl and $R_2$ is (lower alkyl), tetrazole or (lower alkyl)thiadiazole.

7. A compound as in claim 1 wherein R is hydrogen, $R_1$ is phenyl and $R_2$ is (1-methyl-1H-tetrazol-5-yl).

8. A compound as in claim 1 wherein R is hydrogen; $R_1$ is 2-thienyl; and $R_2$ is 1-methyl-1H-tetrazol-5-yl.

9. A compound as in claim 1 wherein R is hydrogen, $R_1$ is phenyl and $R_2$ is 1-oxopyridin-2-yl.

10. A compound as in claim 1 wherein R is alkali metal; $R_1$ is 2-thienyl; and $R_2$ is (1-methyl-1H-tetrazol)-5-yl.

* * * * *